United States Patent [19]

Piejko et al.

[11] Patent Number: 5,456,861
[45] Date of Patent: Oct. 10, 1995

[54] ABIETIC ACID DERIVATIVES AND THEIR USE AS EMULSIFIERS

[75] Inventors: Karl-Erwin Piejko, Berg.-Gladbach; Dieter Constant, Leverkusen; Christian Lindner, Cologne; Claus Wulff, Krefeld, all of Germany

[73] Assignee: Bayer AG, Leverkusen, Germany

[21] Appl. No.: 510,836

[22] Filed: Apr. 18, 1990

[30] Foreign Application Priority Data

Apr. 26, 1989 [DE] Germany .......................... 39 13 680.9
Aug. 8, 1989 [DE] Germany .......................... 39 26 118.2

[51] Int. Cl.$^6$ .............................. B01F 17/00; C07C 61/29
[52] U.S. Cl. ............................................. 252/356; 562/404
[58] Field of Search ........................... 252/356; 530/225, 530/228, 229; 562/404

[56] References Cited

U.S. PATENT DOCUMENTS

| | | | |
|---|---|---|---|
| 2,329,517 | 9/1943 | Cok ..................................... | 530/225 X |
| 2,434,656 | 1/1948 | Humphrey ............................. | 530/225 |
| 2,511,575 | 6/1950 | Flaherty ................................ | 530/225 |
| 2,580,496 | 1/1952 | Zeiss ..................................... | 530/225 |
| 3,223,696 | 12/1965 | Boylau et al. ....................... | 530/225 X |
| 3,528,959 | 9/1970 | Patrick, Jr. et al. ................ | 526/213 X |
| 3,980,630 | 9/1976 | Ishigami et al. ...................... | 252/356 X |
| 3,992,433 | 11/1976 | Ariyoshi et al. ..................... | 252/367 X |
| 4,104,272 | 8/1978 | Pettelkau ............................. | 252/356 X |

FOREIGN PATENT DOCUMENTS 1079189  8/1967  United Kingdom .................. 530/225

*Primary Examiner*—Gary L. Geist
*Assistant Examiner*—Daniel S. Metzmaier
*Attorney, Agent, or Firm*—Connolly & Hutz

[57] ABSTRACT

Process for pretreating abietic acid derivatives comprising dissolving an abietic derivative in water to form a 2 to 25% by weight solution, adding a base so that the pH of the solution is from 10 to 14 and removing from 0.5 to 25% by weight of the abietic acid derivative originally present in the solution by extraction or steam distillation while maintaining the pH from 10 to 14.

6 Claims, No Drawings

ABIETIC ACID DERIVATIVES AND THEIR USE AS EMULSIFIERS

The invention relates to a process for pretreating abietic acid derivatives and the use of the abietic acid derivatives treated in accordance with the invention as emulsifiers for emulsion polymerisation of olefinic monomers.

Abietic acid derivatives (resin soaps) have good emulsifying properties and favourably influence polymers prepared with their aid, in that residual amounts remaining in the polymer improve the processing properties, such as adhesiveness and injection moulding behaviour.

Abietic acid derivatives (resin soaps) are obtained from wood resins, such as colophonium, which contain terpene compounds of the abietic acid type as main constituents. To obtain emulsifiers which can be used, these resins are normally subjected to hydrogenation or dehydrogenation (see Houben-Weyl "Methoden der organischen Chemie" ("Methods in Organic Chemistry") volume XIV, 4th edition, page 194f, Georg Thieme Verlag, Stuttgart 1961). The modified resin acids thus obtained or salts thereof (abietic acid derivatives) are used on an industrial scale as emulsifiers, for example in the manufacture of cold rubber. They can be obtained commercially under the tradenames such as Dresinate®, Gresinox®.

The abietic acid derivatives can also be used for the preparation of ADS graft polymers, in particular for the preparation of the rubber base for these graft products and as auxiliary emulsifiers for the actual graft polymerisation. ABS graft polymers are prepared to the largest extent and are used as such or mixed with other thermoplastic plastics (polyvinylchloride, polycarbonate), as thermoplastic moulding compositions.

Contaminants are evaporated out from polymers prepared using abietic acid derivatives as emulsifiers, when they are subjected to heat. This phenomenon is generally termed "fogging" because the materials evaporated out from the plastic of the instrument panel has been observed as a coating on the windscreen of motor vehicles.

The abietic acid derivatives used as emulsifiers are complex product mixtures, because they are produced by chemically changing a natural product of complex composition. Even cleaning operations which lead first of all to the known, commercially available products having emulsifier properties which can be utilised, do not prevent "fogging".

The object of the invention is a process for pretreating abietic acid derivatives (resin soaps), which is characterised in that they are dissolved in water with addition of bases and extraction or steam distillation is carried out.

The solution of the abietic acid derivatives can be prepared at 20° to 95° C. at a concentration of 1 wt. % up to saturation, preferably from 2 to 25 wt. %, with addition of bases, such as sodium hydroxide or potassium hydroxide. The pH of the solution is preferably 10 to 14, in particular 11 to 13.

The solution of abietic acid derivatives can be extracted by shaking in known manner using organic media, which are not completely miscible with water, at a temperature of 20° C. up to the boiling point of the organic medium, or can be extracted continuously. The organic media should not be allowed to form stable emulsions using the abietic acid derivative solution, because otherwise the organic phase can no longer be separated. Examples of organic media are alkanes and alkane mixtures, preferably in combination with small amounts of higher alcohols, such as,hexane, cyclohexane, heptane, petroleum ether mixtures having 1 to 10 wt % of butanols, pentanols or hexanols, ethers, such as dibutylether, diethylether, aliphatic esters, such as butyl acetate, propyl acetate, ethyl acetate, and mixtures of these liquids.

Particularly preferred organic media are hexane, cyclohexane and heptane having 1 to 10 wt % of butanols It is possible to use known auxiliaries to separate the organic phase, for example silicone oils.

The pH values of the aqueous phase given above must be maintained during extraction. Low temperatures must be maintained particularly when organic phases are used which may be saponified (for example esters) when using alkali, and optionally the pH value must be corrected by addition of alkaline solution.

When treating the abietic acid derivative solution by steam distillation, the process is preferably carried out in conventional manner by introducing superheated steam while maintaining the initial concentration of abietic acid derivative.

In a preferred embodiment of steam distillation, known phenolic inhibitors, for example sterically hindered phenols, in particular those having molar masses above 200 g/mole, are added in amounts of 10 to 1,000 ppm. The amount of distillate is preferably the same amount to thirty times the amount of solution used.

Extraction and steam distillation must be carried out in accordance with the invention so that the extract, after removing the organic medium, or the steam distillate, contains 0.5 to 25 wt %, preferably 3 to 20 wt %, in particular 5 to 15 wt. %, of the abietic acid derivative originally used.

After treating the abietic acid derivative solution in accordance with the invention, the solubility of the abietic acid derivatives in the alkaline solution can be reduced. However, this is not an obstacle to the use as emulsifier, as the full solubility can be restored by heating, diluting or addition of a dissolving agent. The organic media mentioned above for extraction are examples of suitable dissolving agents. In preferred cases, for example using alkanes, an aqueous phase, which already contains small amounts of the alkanes, is obtained after extraction. This amount is often sufficient to form a clear solution.

It is also possible to remove the emulsifier from the treated solution, for example by lowering the pH or by evaporating the water. The emulsifier can then be dissolved in monomer and introduced in this form for further use in emulsion polymerisation. The amount of base necessary for a good emulsifying effect must then be added separately as aqueous solution. Extraction is the preferred pretreatment.

As the abietic acid derivatives used in accordance with the invention may be completely soluble in the solvents used for extraction, it is surprising that selective removal of certain portions is possible in the extraction of the invention. Obviously the components which cause "fogging" are predominantly removed.

A further object of the invention is the use of the abietic acid derivatives pretreated in accordance with the invention as emulsifiers for emulsion polymerisation of olefinic monomers.

Examples of polymers known per se which may be prepared using the emulsifiers of the invention, are crosslinked and non-cross-linked diene rubbers and acrylate rubbers, for example diene rubbers from butadiene, isoprene, chloroprene, optionally with comonomers, such as styrene and/or acrylonitrile and acrylate rubbers from alkylacrylates optionally with comonomers, such as acrylonitrile, styrene, methylmethacrylate and/or graft polymers of resin-forming monomers on diene rubbers and on acrylate rubbers, for example acrylonitrile/butadiene/styrene polymers, acrylonitrile/styrene/alkylacrylate polymers or methylmethacrylate/butadiene/styrene polymers and/or resin-like polymers of styrene, α-methylstyrene, $C_1$–$C_4$-alkylmethacrylate, $C_1$–$C_4$-vinylcarboxylic acids, acrylonitrile, $C_1$–$C_8$-alkylacrylates and mixtures thereof.

The polymerisation processes using the emulsifiers of the invention are known, as is the working up of the emulsion polymers to give polymer powders and granules.

The emulsifier solutions of the invention may be substituted partly by conventional anionic emulsifiers, such as alkylcarboxylic acids, alkyl sulphonic acids, known abietic acid derivatives etc., in proportions up to 60%, relative to the abietic acid derivatives used, but preferably in proportions smaller than 40%, in the preparation of the polymers.

In multi-stage polymerisation processes, such as for the preparation of graft polymers, those processes are preferred where the proportion of emulsifiers of the invention, particularly in the final steps of the process, is greater than 70%, in particular greater than 90%, when emulsifiers which are not of the invention are co-used.

The emulsion polymers of the invention are worked up to give powders in accordance with conventional methods, for example by coagulation, spray drying or evaporative processes. The resulting polymer powders have improved processing and use properties on their own or in combination with other thermoplastics, as fewer volatile portions are evaporated out during processing in the melt or from the finished moulding, and hence there are fewer machine coatings, reduced smell pollution, or fewer coatings on the inner sides of windows, for example when applied to a motor vehicle, i.e. prevents "fogging".

EXAMPLES

1. Preparation of abietic acid derivative solutions of the invention

The products (sodium salt, 70% strength in water) which can be obtained under the tradenames Dresinate® 731 and Gresinox® 578M were used as abietic acid derivatives.

1.1 Extraction using hexane/i-butanol

A A solution of 240 g of Dresinate® 731, 20 g of sodium hydroxide (solid) in 2,400 g of water is extracted by shaking using a mixture of 710 g of hexane and 43 g of i-butanol. The aqueous phase (solution 1.1.A) has a pH of 12.6. The organic phase contains 12.5 g of extract.

B 1,650 g of an aqueous phase treated analogously to A are extracted by shaking two further times using 650 g of a mixture of hexane with 4% of i-butanol each time. The resulting aqueous phase (solution 1.1.B) has a pH of 12.6. The combined organic phases contain 1.55 g of extract.

The fact that only small amounts of extract are obtained in the second extraction process using increased amounts of organic phase, shows that only certain portions of the emulsifier mixture are extracted in the process of the invention, the extraction is therefore selective.

1.2 Extraction using ethyl acetate

A solution of 240 g of Dresinate® 731, 20 g of sodium hydroxide (solid) in 2,400 g of water is extracted by shaking using 1.1 litres of ethyl acetate. The aqueous phase is then partially distilled on a rotary evaporator at 70° C. (amount of distillate 400 ml). The pH of the resulting aqueous phase is still only 8.8. 8.6 g of 1 sodium hydroxide are added per 100 g of solution for further use as emulsifier solution. The resulting aqueous solution (solution 1.2) has a pH of 12. The organic phase contains 22.7 g of extract.

1.3 Steam distillation 240 g of Dresinate® 731, 20 g of sodium hydroxide (solid) and 480 mg of 2,2'-methylene-bis-(4-methyl-6-cyclohexylphenol) are dissolved in 700 g of water at 70° C. and subjected to steam distillation, so that the volume in the sump receiver remains approximately constant. It is distilled until about 6.5 litres of water have passed over as distillate. The residue is diluted with water to give a 10% strength solution of Dresinate® (solution 1.3). The pH of the solution is 12.6. The distillate is extracted using ethylacetate; the amount of solid extract is 7.2 g.

2. Preparation of novel and comparative graft polymers of the ABS type

The following are placed in a reactor: 896 g of water, 303 g of a polybutadiene rubber latex having a solids content of 49.5 wt. % and an average particle diameter ($d_{50}$) of 390 nm and 355 g of a polybutadiene rubber latex having a solids content of 42.3 wt. % and an average particle diameter ($d_{50}$) of 130 nm. (These polybutadienes were prepared using Dresinate® as emulsifier.) The reactor is flushed with nitrogen for 15 minutes. After heating at 65° C., a solution of 7.9 g of potassium peroxodisulphate in 286 g of water is added under a gentle stream of nitrogen. The following solutions are then introduced into the reactor uniformly in the course of 7 hours:

Solution 1:
    462 g of styrene
    238 g of acrylonitrile

Solution 2:
    Emulsifier solution, composition see Table 1.

The mixture is allowed to polymerise for 6 hours at 65° C., 1 wt. % (relative to solids) of 2,2'-methylene-bis-(4-methyl-6-cyclohexylphenol) is added and the latex is coagulated using an aqueous magnesium sulphate solution. The coagulate is washed with water and dried at 60° C. to a residual moisture <0.5%.

3. Testing the properties

The powders obtained in accordance with 2. are subjected to a fogging test (window fogging test; 3 hours at 100° C.) in accordance with DIN 75201. The results are also listed in Table 1.

TABLE 1

Composition of the emulsifier solution (Solution 2) for the preparation of ABS graft polymers and gloss values of the corresponding powders from fogging measurements

| Example No. | Solution 2 Type/Amount | Gloss values in % |
|---|---|---|
| 1 | Example 1.1.A/367 g | 91 |
| 2 | Example 1.1.B/382 g | 93 |
| 3 | Example 1.2/251 g + 70 g of water | 91 |
| 4 | Example 1.3/227 g + 100 g of water | 88 |
| 5* | Dresinate 731 ® 31.3 g + 220 g of water + 74 g of 1N NaOH | 78 |
| 6* | Gresinox 578M ® 21.9 g + 230 g of water + 74 g of 1N NaOH | 85 |

*= Comparative tests

The gloss values in Table 1 show that emulsion polymers of the ABS type having reduced volatile portions can be prepared using the emulsifier solutions of the invention. Mouldings manufactured therefrom are also characterised by reduced volatile portions.

We claim:

1. Process for pretreating abietic acid derivatives comprising dissolving an abietic derivative in water to form a 2 to 25% by weight solution, adding a base so that the pH of the solution is from 10 to 14 and removing from 0.5 to 25% by weight of the abietic acid derivative originally present in the solution by steam distillation while maintaining the pH from 10 to 14.

2. Process according to claim 1 wherein the abietic acid derivatives are resin soaps.

3. Process according to claim 1 wherein the abietic acid derivative is obtained from wood resins containing terpene compounds.

4. Process for the emulsion polymerization of olefinic monomers comprising polymerizing said monomers in the presence of an emulsifier comprising the abietic acid derivative treated by the process according to claim 1.

5. Process according to claim 4 wherein the olefinic monomers are diene monomers, styrene, acrylonitrile, $C_1$–$C_8$ alkylacrylates or mixtures thereof.

6. Process according to claim 5 wherein the diene monomers are butadiene, isoprene or chloroprene.

* * * * *